United States Patent
Suda et al.

(10) Patent No.: US 8,277,834 B2
(45) Date of Patent: Oct. 2, 2012

(54) METHOD FOR PRODUCING PROTEIN ADSORPTION-PREVENTING OCULAR LENS MATERIAL

(75) Inventors: Yukimitsu Suda, Yokohama (JP);
Kazuyuki Miyazawa, Yokohama (JP);
Kazuhiko Ishihara, Mitaka (JP)

(73) Assignees: Shiseido Company, Ltd., Tokyo (JP);
Kazuhiko Ishihara, Tokyo (JP)

( * ) Notice: Subject to any disclaimer, the term of this patent is extended or adjusted under 35 U.S.C. 154(b) by 1145 days.

(21) Appl. No.: 10/592,772

(22) PCT Filed: May 18, 2005

(86) PCT No.: PCT/JP2005/009083
§ 371 (c)(1),
(2), (4) Date: May 5, 2007

(87) PCT Pub. No.: WO2005/114305
PCT Pub. Date: Dec. 1, 2005

(65) Prior Publication Data
US 2008/0038221 A1    Feb. 14, 2008

(30) Foreign Application Priority Data

May 24, 2004  (JP) ................................. 2004-153256
May 10, 2005  (JP) ................................. 2005-136847

(51) Int. Cl.
*A61K 31/80*  (2006.01)
(52) U.S. Cl. .................... 424/427; 424/1.77; 424/78.12; 424/429
(58) Field of Classification Search ............... 525/328.2, 525/328.8, 330.4, 340
See application file for complete search history.

(56) References Cited

U.S. PATENT DOCUMENTS 5,308,641 A * 5/1994 Cahalan et al. ................. 427/2.1
5,422,402 A * 6/1995 Bowers et al. ............. 525/328.2
* cited by examiner

*Primary Examiner* — Walter Webb

(57) ABSTRACT

The present invention is a method of manufacturing an eye lens material having a process in which a phosphorylcholine group-containing chemical compound represented by the following formula (1) is reacted and covalently bonded onto the surface of an eye lens material wherein a chemical compound having an end amino group is introduced to said eye lens material and then the chemical compound represented by the following formula (2) or (3) is introduced through said chemical compound having an end amino group.

The object of the present invention is to provide a method of manufacturing a contact lens that prevents protein adsorption.

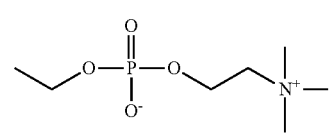

(1)

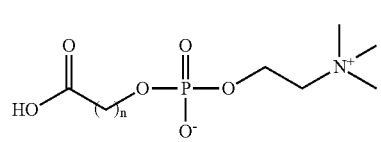

(2)

n denotes a natural number 1-18.

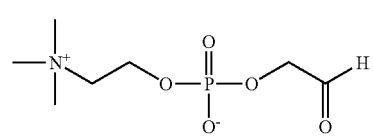

(3)

4 Claims, 1 Drawing Sheet

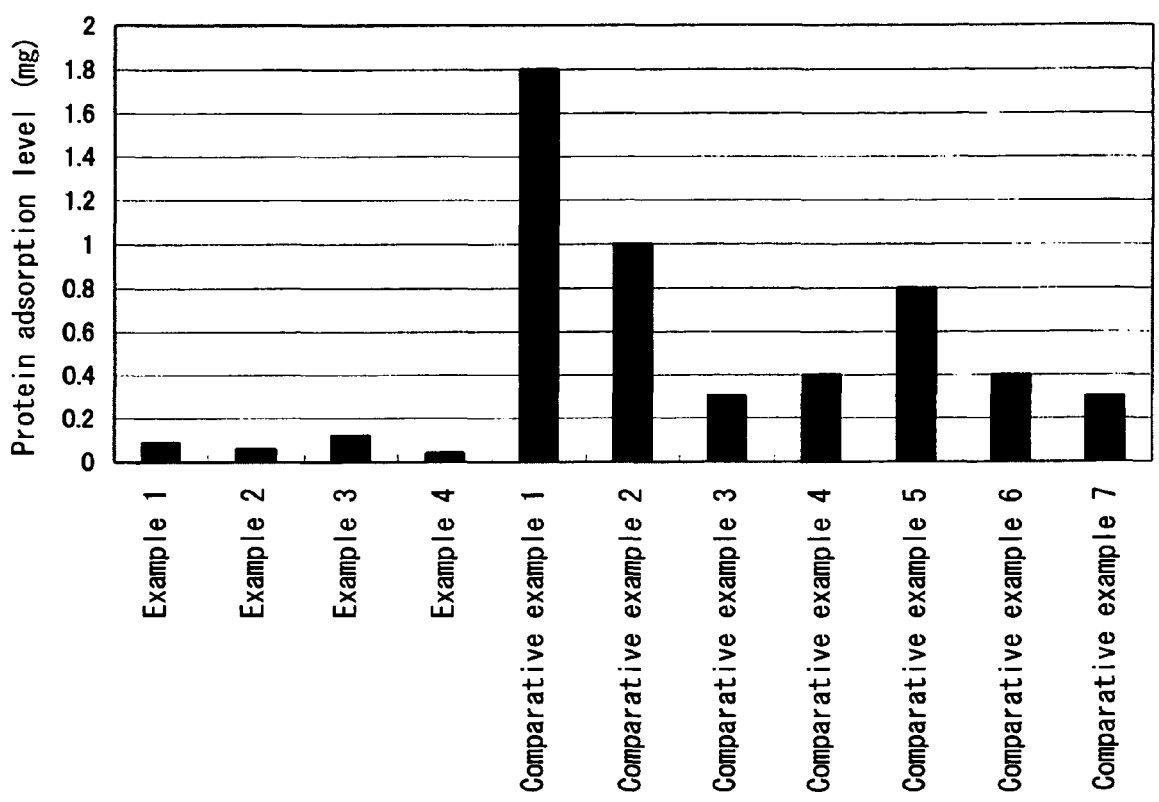

US 8,277,834 B2

METHOD FOR PRODUCING PROTEIN ADSORPTION-PREVENTING OCULAR LENS MATERIAL

TECHNICAL FIELD

The present invention relates to a method of manufacturing an eye lens material for contact lenses and such and a method of preventing protein adsorption. More specifically, it relates to a method of preventing protein stains by treating the surface of an eye lens material (particularly for contact lenses) by means of an after-treatment using a phosphorylcholine group-containing chemical compound.

BACKGROUND ART

The practice of polymerizing phosphorylcholine group-containing monomers for use as a contact lens material is a prior art (Patent Documents 1-3). For example, Patent Document 1 discloses a moist soft contact lens containing a phosphorylcholine group-containing (meth)acrylic ester as a constitutional unit; it is described as having superior moisture content, oxygen permeability, and tensile strength, as well as reduced protein adsorption and the ability to suppress stain adhesion.

As an example of an after-treatment method for contact lenses, Patent Document 4 describes polymerization of phosphorylcholine group-containing monomers on the contact lens surface to prepare a contact lens having hydrophilic surfaces and reduced protein adsorption.

In addition, Patent Document 5 describes a reduction in protein adsorption by chemically bonding a low molecular weight phosphorylcholine compound onto the contact lens surface.

Example 5 in Patent Document 5 describes a method of introducing phosphorylcholine groups onto the surface of a contact lens composed of a hydroxyethyl methacrylate copolymer by treating glycerophosphorylcholine with 1,1'-carbonyldiimidazole. However, the target phosphorylcholine-treated contact lens could not be obtained as a result of an attempt to duplicate the reaction described above.

Also, reaction formula 6 in Patent Document 6 lists a chemical structure formula that represents an active ester derived from a phosphorylcholine carboxyl derivative. Since there is no mention of a synthesis method nor Examples of the phosphorylcholine carboxyl derivative having the structure described, it is not possible to attempt to duplicate the process; however, if it were to be synthesized based on ordinary organic chemistry commonsense, the method would be very cumbersome and the yield would be low, indicating little practical use.

As mentioned above, the treatment method described in Patent Document 5 does not describe the synthesis method of the carboxyl group-containing phosphorylcholine-containing chemical compound for treating the contact lens; therefore there is no way to directly implement the described method. Also, the reaction to introduce phosphorylcholine groups onto the contact lens surface, under the conditions described in these Patent Documents, does not proceed sufficiently and results in a low introduction level, and therefore a superior protein adsorption prevention effect is not achieved.

Stains on a contact lens result from adsorption of proteins and/or lipids contained in lacrimal fluid; these stains can cause eye troubles such as allergies and infections (Non-patent Document 1). Protein stains cause a fatal problem particularly for a moist contact lens whose main ingredient is a 2-hydroxyethyl methacrylate polymer, a highly moist soft contact lens prepared by copolymerizing this ingredient with a small amount of methacrylic acid, which is an ionic monomer, and a soft contact lens whose main ingredient is a polymer of a hydrophilic monomer such as N-vinyl pyrrolidone and N,N-dimethyl acrylamide.

Patent Document 1: Japanese Patent Laid-Open H10-177152 bulletin

Patent Document 2: Japanese Patent Laid-Open 2000-111847 bulletin

Patent Document 3: Japanese Patent Laid-Open 2000-169526 bulletin

Patent Document 4: Japanese Patent Laid-Open 2001-337298 bulletin

Patent Document 5: Japanese Patent Laid-Open H5-505121 bulletin

Non-patent Document 1: "Stains on soft contact lenses and analysis thereof", Material Stage, Vol. 4, No. 1, 2004

DISCLOSURE OF INVENTION

Problem that the Present Invention Aims to Solve

The present invention provides a contact lens that prevents protein stains by suppressing protein adsorption on the contact lens by means of an after-treatment in which phosphorylcholine groups are covalently bonded onto the contact lens surface via a chemical compound having an end amino group.

That is, the present invention does not prepare a protein adsorption prevention contact lens by polymerizing monomers having phosphorylcholine groups, as in the methods described in Patent Documents 1-3 above; its object is to give contact lenses a superior protein adsorption prevention function by means of an after-treatment.

Also, the present invention does not introduce phosphorylcholine groups by polymerizing phosphorylcholine-containing monomers onto the contact lens surface to coat it with a polymer different from the contact lens itself, as in a method described in Patent Document 4; it uses direct covalent bonding of phosphorylcholine groups, rather than polymer coating, and thus aims to achieve a superior protein adsorption prevention effect without changing the original characteristics of the contact lens with polymer coating.

Furthermore, the present invention aims to achieve a superior protein adsorption prevention effect by introducing a sufficient amount of phosphorylcholine, as opposed to the method described in Reference 5, which is shown to be incapable of introducing a sufficient amount of phosphorylcholine groups onto the contact lens surface when an attempt to duplicate this method is actually made.

In particular, the essential difference between the present invention and the method shown in Patent Document 5 lies in the fact that the present invention introduces a chemical compound having an end amino group onto the surface of an eye lens material, through which the low molecular weight phosphorylcholine group-containing chemical compound of formula (2) or (3) is chemically bonded onto the contact lens surface. This makes it possible to suppress protein adsorption efficiently while controlling lens deformation. That is, when phosphorylcholine groups are directly introduced to the functional groups present on the contact lens surface, the lens tends to expand a little due to their high hydrophilicity; however, this expansion can be easily controlled if an alkyl group or oxyalkyl group having an amino group on both ends is introduced between the lens surface and the phosphorylcholine group. The lower the hydrophilicity of the chemical compound having an amino group, the higher the effect of controlling the lens expansion. The expansion is most preferably controlled when the length of the alkyl chain is 0-6. In the case of an oxyethylene group, the effect of the chain length is small.

[Means to Solve the Problem]

That is, the present invention provides a method of manufacturing an eye lens material having a process in which a phosphorylcholine group-containing chemical compound represented by the following formula (1) is reacted and covalently bonded onto the surface of an eye lens material wherein a chemical compound having an end amino group is introduced to said eye lens material and then the chemical compound represented by the following formula (2) is introduced through said chemical compound having an end amino group.

[Chemical formula 5]

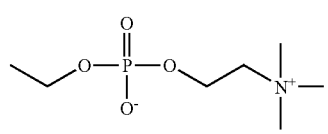
(1)

[Chemical formula 6]

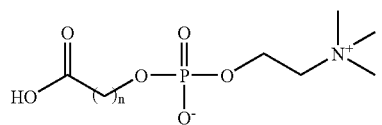
(2)

n denotes a natural number 1-18.

Also, the present invention provides a method of manufacturing an eye lens material having a process in which a phosphorylcholine group-containing chemical compound represented by the following formula (1) is reacted and covalently bonded onto the surface of an eye lens material wherein a chemical compound having an end amino group is introduced to the surface of said eye lens material and then the phosphorylcholine group-containing chemical compound represented by the following formula (3) is introduced through said chemical compound having an end amino group.

[Chemical formula 7]

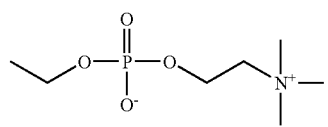
(1)

[Chemical formula 8]

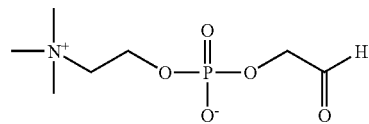
(3)

Furthermore, the present invention provides the aforementioned method of manufacturing an eye lens material wherein said chemical compound having an end amino group is a chemical compound having an alkyl group of C0(hydrazine)-C12, an ethylene oxide group with a degree of polymerization of 1-10, a propyleneoxide group with a degree of polymerization of 1-10, an ethyleneimine with a degree of polymerization of 1-20, or a propyleneimine with a degree of polymerization of 1-20, or a chemical compound having aniline, or piperazine.

Also, the present invention provides a protein adsorption prevention method for an eye lens material wherein protein adsorption on the eye lens material is prevented by covalently bonding phosphorylcholine groups onto the eye lens material surface by means of an after-treatment in which a chemical compound having an end amino group is introduced onto the surface of the eye lens material and then the aforementioned phosphorylcholine group-containing chemical compound is reacted with the eye lens material.

Also, the present invention provides a protein adsorption prevention method for an eye lens material wherein protein adsorption on the eye lens material is prevented by covalently bonding phosphorylcholine groups onto the eye lens material surface by means of an after-treatment in which amino groups are introduced to the phosphorylcholine group-containing chemical compound of said formula (2) or (3), which is then reacted with the eye lens material.

Also, the present invention provides an eye lens material wherein a spacer is introduced by means of amide bonding or alkylamine bonding between the surface of the eye lens material and the chemical compound having a phosphorylcholine group of said formula (2) or (3) to be introduced.

[Effects of the invention]

The manufacturing method of the present invention uses a simple after-treatment method to covalently bond any amount of phosphorylcholine groups onto the eye lens material surface through a chemical compound having an end amino group.

The eye lens material of the present invention is a contact lens onto whose surface phosphorylcholine groups are covalently bonded through a chemical compound having an end amino group and therefore it effectively suppresses protein adsorption on the contact lens and achieves a superior stain prevention effect. It can also improve moisture retention and the sensation of wearing the contact lens.

Also, since the protein adsorption prevention function can be added by means of an after-treatment, the present invention can be easily used on existing contact lenses.

Since polymer coating is not used as the method to introduce the phosphorylcholine groups, durability is superior and the original characteristics of the contact lens are essentially not degraded.

The contact lens obtained by the present invention is a contact lens that gives a superior sensation when it is worn. Therefore it can be preferably used in situations where wearing contact lenses tends to feel like a foreign body is touching the eye due to reasons such as poor flexibility of the material.

In particular, the reaction between the chemical compound having an end amino group and the chemical compound of formula (2) and (3) has a very high yield and allows easy control of the amount to be introduced. Therefore, the present invention has the superior effect of very efficiently introducing the phosphorylcholine group of formula (1) onto the contact lens surface.

Also, this method can efficiently suppress protein adsorption while controlling lens deformation. That is, when highly hydrophilic functional groups are directly introduced to the functional groups present on the contact lens surface, the lens tends to expand a little; however, this expansion can be easily controlled if a functional group having an amino group on both ends is introduced between the lens surface and the phosphorylcholine group and its polarity is controlled.

BRIEF DESCRIPTION OF DRAWINGS

FIG. 1 is a graph showing protein adsorption on the contact lenses of Examples and Comparative examples.

BEST MODE FOR CARRYING OUT THE INVENTION

The present invention is described in detail below.
"The Chemical Compound Having an End Amino Group"

Examples of the chemical compound used in the present invention include hydrazine, ethylenediamine, propylenediamine, 1,4-diaminobutane, 1,6-diaminohexane, piperazine, ethyleneglycolbis(2-aminoethyl)ether, and ethyleneglycolbis(3-aminopropyl)ether, any of which can be purchased as a reagent. Also, the polarity is in an appropriate range for preventing expansion. Also, chemical compounds having three or more end amino groups such as tris(2-aminoethyl) amine and amino end group dendrimers are valid for the chemical compound having an end amino group used in the present invention.
"A Method of Preparing the Phosphorylcholine Group-Containing Chemical Compound of Formula (2)"

A phosphorylcholine group can be synthesized by means of total synthesis. However, the synthesis conditions are cumbersome, a strict moisture-free condition is required, and therefore the manufacturing cost is high.

On the other hand, phosphorylcholine can be extracted as lecithin, which is a constituent component of cell membranes; by removing the fatty acid portion by means of hydrolysis, phosphorylcholine can be easily obtained at low cost in the form of 1-α-glycerophosphorylcholine. The inventors discovered that a phosphorylcholine group-containing chemical compound can easily be obtained by means of oxidative cleavage of the diol portion of this 1-α-glycerophosphorylcholine.

The most representative synthesis method oxidizes 1-α-glycerophosphorylcholine by using sodium periodate and ruthenium trichloride in a solvent such as water and acetonitrile to obtain the target carboxyl derivative.

For the chemical compound of formula (2), it is preferable to use carboxymethyl phosphorylcholine (n=1) obtained by the oxidative cleavage of 1-α-glycerophosphorylcholine.

"A Method of Preparing Carboxymethyl Phosphorylcholine by Means of the Oxidative Cleavage of 1-α-Glycerophosphorylcholine"

1-α-glycerophosphorylcholine can be converted into carboxymethyl phosphorylcholine by means of the oxidative cleavage using periodate and ruthenium trichloride in a water/acetonitrile mixed solvent.

That is, as shown in Examples, 5 g of 1-α-glycerophosphorylcholine is dissolved in water (70 ml)/acetonitrile (30 ml). As the temperature is lowered with ice, 17 g of sodium periodate and 80 mg of ruthenium trichloride are added, followed by overnight stirring. The precipitate is filtered, concentrated under a reduced pressure, and extracted with methanol to obtain 3.86 g (yield 82%) of the target carboxymethyl phosphorylcholine.
"A Method of Preparing the Phosphorylcholine Group-Containing Chemical Compound of Formula (3)"

Oxidative cleavage of a prior art glycerophosphorylcholine is carried out by means of a prior art method. For example, 1,2-diol is oxidized with an oxidant such as periodic acid, periodate, or bismuth trioxide to cleave the bond and obtain an aldehyde derivative. The reaction is usually carried out in water or an organic solvent containing water at a reaction temperature between 0° C. and room temperature. The aldehyde derivative may go through an equilibrium reaction in water to become a hydrate, but this does not affect the subsequent reaction with the amine. An example of a scheme for preparing a monofunctional aldehyde derivative containing a phosphorylcholine group is described below.

[Chemical formula 13]

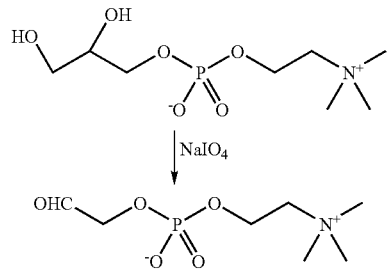

"An Eye Lens Material"

The eye lens material in the present invention refers to a molded piece of a material that is worn in the eye. It mainly refers to a contact lens. A contact lens of any material can be used. The contact lens of the present invention can be prepared from a contact lens comprising a polymer such as methacrylic acid (MAA), acrylic acid (AA), 2-hydroxyethyl methacrylate (HEMA), N-vinylpyrrolidone (NVP), N,N-dimethylacrylamide (DMAA), vinyl alcohol (VA), methyl methacrylate (MMA), trifluoroethyl methacrylate (TFEMA), cellulose acetate butyrate (CAB), fluoro silicone, hexafluoroisopropyl methacrylate, perfluoroalkyl methacrylate, siloxanyl methacrylate (SiMA), siloxanyl styrene (SiSt), ethylene glycol dimethacrylate (EGDMA), allyl methacrylate (AMA), and silicone macromers, as well as a copolymer of two or more types of monomers.

A soft contact lens that uses 2-hydroxyethyl methacrylate as the main constituent ingredient and an ionic soft contact lens prepared by copolymerizing it with methacrylic acid are representative soft contact lenses; these contact lenses are susceptible to protein adsorption. Therefore, they are preferably treated with the method of the present invention.

A preferable monomer for the present invention is acrylic acid or methacrylic acid. When the constituent monomers of a contact lens include acrylic acid or methacrylic acid, the surface of the contact lens has carboxyl groups, which makes it possible to easily introduce said chemical compound having an amino group on both ends by means of amide bonding.

For a contact lens that doesn't have carboxyl groups, a surface modifier and/or plasma treatment can be used to introduce carboxyl groups. A specific introduction method using plasma is described below.
<Introduction of Carboxyl Groups by Means of a Surface Reaction Via a Plasma Treatment>

In a carbon dioxide atmosphere, low temperature plasma is used to introduce carboxyl groups onto the contact lens surface. Specifically, the contact lens is put into a plasma reactor vessel and, after a vacuum pump is used to form a vacuum in the reactor vessel, carbon dioxide is introduced. Carboxyl groups can then be introduced onto the contact lens surface by means of glow discharge.
"Preparation Method"

Carboxyl groups of the constituent monomers are used for this method, or carboxyl groups are newly introduced onto the contact lens surface by means of a plasma treatment and such; the chemical compound having an end amino group is then covalently bonded (amide bonding) with a conventional method.

Specifically, a contact lens made of poly-HEMA is put into a plasma reactor vessel (BP-1 from Samco International Laboratories); all the air in the vessel is then replaced by carbon dioxide and an anode treatment (RF Power 100) is carried out at room temperature for 10 minutes to introduce carboxyl groups. Next, the contact lens is treated in the presence of a carbodiimide type coupling agent such as carbonyldiimidazole and 1-ethyl-3-(3-dimethylaminopropyl)carbodiimide hydrochloride, or thionyl chloride, phosphorus pentachloride, phosphorus oxychloride, phosphorus tribromide, or oxalyl chloride and then immersed in water or an organic solvent containing an excess amount of the chemical compound having an amino group on both ends to carry out amidation, thus introducing amino groups onto the ends, followed by rinsing.

Next, the chemical compound of formula (2) or (3) is amide-bonded to the unreacted amino groups.

Specifically, in the case of the chemical compound of formula (2), the chemical compound of formula (2) is dissolved or dispersed in water or an organic solvent such as N,N-dimethylformamide, acetonitrile, or dimethylsulfoxide; then a carbodiimide type coupling agent such as carbonyldiimidazole and 1-ethyl-3-(3-dimethylaminopropyl)carbodiimide hydrochloride, or thionyl chloride is added to obtain an active ester or acid chloride, which then is amidated with the amino groups on the contact lens surface.

In the case of the chemical compound of formula (3), the chemical compound of formula (3) is dissolved in water or a protic solvent such as methanol or a solvent containing it, in which the contact lens is immersed and reacted for four hours; sodium cyanoborohydride is then added, followed by overnight stirring and rinsing.

As a result, the phosphorylcholine group of formula (1) can be introduced onto the contact lens surface through the chemical compound having an end amino group.

In terms of introducing the chemical compound having an end amino group, any of those listed can be reacted under the same conditions.

Also, amino groups can be directly introduced onto the contact lens by means of a plasma treatment. A prior art method is described below.

<Introduction of Amino Groups by Means of a Surface Reaction Via a Plasma Treatment>

Amino groups are introduced onto the contact lens surface by means of a low temperature plasma in a nitrogen gas atmosphere. Specifically, a contact lens is put into a plasma reactor vessel and, after a vacuum pump is used to form a vacuum in the reactor vessel, nitrogen gas is introduced. Amino groups can be then introduced onto the lens surface by means of glow discharge. References related to the plasma treatment are shown below:

1. M. Muller, C. oehr Plasma aminofunctionalisation of PVDF microfiltration membranes: comparison of the in plasma modifications with a grafting method using ESCA and an amino-selective fluorescent probe Surface and Coatings Technology 116-119 (1999) 802-807
2. Lidija Tusek, Mirko Nitschke, Carsten Werner, Karin Stana-Kleinschek, Volker Ribitsch Surface characterization of NH3 plasma treated polyamide 6 foils Colloids and Surfaces A: Physicochem. Eng. Aspects 195 (2001) 81-95
3. Fabienne Poncin-Epaillard, Jean-Claude Brosse, Thierry Falher Reactivity of surface groups formed onto a plasma treated poly(propylene) film Macromol. Chem. Phys. 200. 989-996 (1999)

EXAMPLES

Next, the present invention is described in detail by referring to Examples. The present invention is not limited to these Examples.

"Synthesis of the Chemical Compound of Formula (2)"

5 g of 1-α-glycerophosphorylcholine was dissolved in water (70 ml)/acetonitrile (30 ml). As the temperature was lowered with ice, 17 g of sodium periodate and 80 mg of ruthenium trichloride were added, followed by overnight stirring. The precipitate was filtered, concentrated under a reduced pressure, and extracted with methanol to obtain 3.86 g (yield 82%) of the target carboxymethyl phosphorylcholine.

Carboxymethyl phosphorylcholine is the chemical compound of formula (2) for n=1.

"Synthesis of the Chemical Compound of Formula (3)"

1-α-glycerophosphorylcholine (450 mg) was dissolved in 15 ml of distilled water and cooled in an ice water bath. Sodium periodate (750 mg) was added, followed by five hours of stirring. The reaction fluid was concentrated under reduced pressure and dried under reduced pressure; methanol was then used to extract the target substance.

Example 1

A Contact Lens Having the Chemical Compound of Formula (2) (Spacer: Ethylenediamine)

A commercially available contact lens EtafilconA (product name: 1-Day Acuvue from J & J, constituent monomer: HEMA-MAA) was immersed in 3 ml of water; then 30 mg of ethylenediamine, 10 mg of 1-ethyl-3-(3-dimethylaminopropyl)carbodiimide hydrochloride, and 6 mg of N-hydroxysuccineimide were added, followed by three hours of stirring at room temperature. After the contact lens was thoroughly rinsed with pure water and immersed in 3 ml of water, 10 mg of the chemical compound of formula (2), 10 mg of 1-ethyl-3-(3-dimethylaminopropyl)carbodiimide hydrochloride, and 6 mg of N-hydroxysuccineimide were added, followed by three hours of stirring at room temperature and thorough rinsing with water to obtain the target contact lens to whose surface phosphorylcholine groups are chemically bonded.

Example 2

A Contact Lens Having the Chemical Compound of Formula (3) (Spacer: Ethylenediamine)>

A commercially available contact lens EtafilconA (product name: 1-Day Acuvue from J & J, constituent monomer: HEMA-MAA) was immersed in 3 ml of water; then 30 mg of ethylenediamine, 10 mg of 1-ethyl-3-(3-dimethylaminopropyl)carbodiimide hydrochloride, and 6 mg of N-hydroxysuccineimide were added, followed by three hours of stirring at room temperature. After the contact lens was thoroughly rinsed with pure water and immersed in 3 ml of water, 10 mg of the chemical compound of formula (3) was added, followed by four hours of stirring at room temperature; then 3 mg of sodium cyanoborohydride was added, followed by overnight stirring and thorough rinsing with water to obtain the target contact lens to whose surface phosphorylcholine groups are chemically bonded.

Example 3

A Contact Lens Having the Chemical Compound of Formula (2) (Spacer: 1,6-Diaminohexane)

A commercially available contact lens EtafilconA (product name: 1-Day Acuvue from J & J, constituent monomer: HEMA-MAA) was immersed in 3 ml of N,N-dimethylformamide; then 50 mg of 1,6-diaminohexane, 10 mg of 1-ethyl-3-(3-dimethylaminopropyl)carbodiimide hydrochloride, and 6 mg of N-hydroxysuccineimide were added, followed by three hours of stirring at room temperature. After the contact lens was thoroughly rinsed with N,N-dimethylformamide and then immersed in 3 ml of N,N-dimethylformamide, it was mixed with a solution prepared by stirring 10 mg of the chemical compound of formula (2) and 6 mg of thionyl chloride in N,N-dimethylformamide for 30 minutes, followed by four hours of reaction time and thorough water rinsing to obtain the target contact lens to whose surface phosphorylcholine groups are chemically bonded.

Example 4

A Contact Lens Having the Chemical Compound of Formula (2) (Spacer: Ethyleneglycolbis (2-Aminoethyl)Ether)

A commercially available contact lens EtafilconA (product name: 1-Day Acuvue from J & J, constituent monomer: HEMA-MAA) was immersed in 3 ml of N,N-dimethylformamide; then 62 mg of ethyleneglycolbis(2-aminoethyl) ether, 10 mg of 2-ethyl-3-(3-dimethylaminopropyl)carbodiimide hydrochloride, and 6 mg of N-hydroxysuccineimide were added, followed by three hours of stirring at room temperature. After the contact lens was thoroughly rinsed with N,N-dimethylformamide and then immersed in 3 ml of N,N-dimethylformamide, it was mixed with a solution prepared by stirring 10 mg of the chemical compound of formula (2) and 6 mg of thionyl chloride in N,N-dimethylformamide for 30 minutes, followed by four hours of reaction time and thorough water rinsing to obtain the target contact lens to whose surface phosphorylcholine groups are chemically bonded.

Comparative Examples 1-5

For comparison, the following commercially available contact lenses were used.
Comparative example 1: EtafilconA (product name: 1-Day Acuvue from J & J)
Comparative example 2: EtafilconA (product name: 1 Day Aquair from Ocular Science)
Comparative example 3: NelfilconA (Focus Dailies from Ciba Vision)
Comparative example 4: Polymacon (product name: Medalist from Bausch & Lomb)
Comparative example 5: VifilconA (Focus from Ciba Vision)
Comparative example 6: Comparative example 1
Comparative example 7: Comparative example 2

Comparative Example 6

Based on the technique described in Patent Document 5, 10 mg of 1-α-glycerophosphorylcholine, 20 mg of 1,1-carbonyldiimidazole, and 20 mg of triethylamine were added to 3 ml of dimethylsulfoxide, followed by two hours of stirring at 50° C. Polymacon, which was used in Example 1, was immersed in this solution, followed by 12 hours of reaction time at room temperature. The contact lens was thoroughly rinsed with dimethylsulfoxide and then with water; the phosphorus quantification showed the level of the introduced phosphorylcholine group to be at the detection limit, 0.0001 micromol/mg, or less, indicating that the reaction did not proceed.

Comparative Example 7

Based on the technique described in Patent Document 5, 10 mg of 1-α-glycerophosphorylcholine, 20 mg of 1,1-carbonyldiimidazole, and 20 mg of triethylamine were added to 3 ml of dimethylsulfoxide, followed by two hours of stirring at 50° C. NelfilconA, which was used in Example 2, was immersed in this solution, followed by 12 hours of reaction time at room temperature. The contact lens was thoroughly rinsed with dimethylsulfoxide and then with water; the phosphorus quantification showed the level of the introduced phosphorylcholine group to be at the detection limit, 0.0001 micromol/mg, or less, indicating that the reaction did not proceed.

FIG. 1 shows the results of protein adsorption for Examples 1-4 and Comparative examples 1-7. These results indicate that the contact lenses of the present invention significantly suppress protein adsorption.

INDUSTRIAL APPLICABILITY

The present invention can highly suppress protein adsorption on contact lenses and significantly prevent stains due to proteins.
The method of the present invention can be preferably used for soft contact lenses, for which protein staining is a fatal problem. It can be preferably used in particular for ionic soft contact lenses, which accelerate protein adsorption.

The invention claimed is:
1. A method of manufacturing an eye lens material which efficiently suppresses protein adsorption while controlling lens deformation, comprising a process in which a phosphorylcholine group-containing chemical compound represented by the following formula (1) is reacted and covalently bonded onto the surface of an eye lens material formed from a polymer of 2-hydroxyethyl methacrylate and methacrylic acid, wherein:
ethylenediamine is introduced to said eye lens material, and then
carboxymethyl phosphorylcholine represented by the following formula (2) is introduced to said eye lens material through said ethylenediamine:

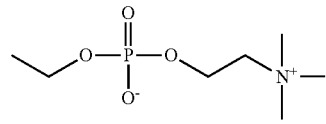
(1)

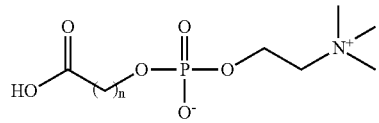
(2)

wherein n denotes a natural number 1-18.

2. A protein adsorption suppression method which controls lens deformation for an eye lens material formed from a polymer of 2-hydroxyethyl methacrylate and methacrylic acid, wherein protein adsorption on the eye lens material is suppressed by covalently bonding phosphorylcholine groups onto the eye lens material surface by means of an after-treatment in which ethylenediamine is introduced onto the surface of the eye lens material, and then the phosphorylcholine group-containing chemical compound of said formula (2) of claim 1 is reacted with said eye lens material.

3. A protein adsorption suppression method which controls lens deformation for an eye lens material formed from a polymer of 2-hydroxyethyl methacrylate and methacrylic acid, wherein protein adsorption on the eye lens material is suppressed by covalently bonding phosphorylcholine groups onto the eye lens material surface by means of an after-treatment in which amino groups are introduced to the phosphorylcholine group-containing chemical compound of said formula (2) of claim 1, which is then reacted with said eye lens material.

4. An eye lens material formed from a polymer of 2-hydroxyethyl methacrylate and methacrylic acid, wherein a spacer is introduced by means of amide bonding or alkylamine bonding between the surface of said eye lens material and the chemical compound having a phosphorylcholine group of said formula (2) of claim 1 to be introduced which efficiently suppresses protein adsorption while controlling lens deformation.

* * * * *